(12) United States Patent
Monfray et al.

(10) Patent No.: US 10,074,649 B2
(45) Date of Patent: Sep. 11, 2018

(54) HIGH-SENSITIVITY ELECTRONIC DETECTOR

(71) Applicant: STMicroelectronics (Crolles 2) SAS, Crolles (FR)

(72) Inventors: Stephane Monfray, Eybens (FR); Gaspard Hiblot, Brignoud (FR)

(73) Assignee: STMicroelectronics (Crolles 2) SAS, Crolles (FR)

( * ) Notice: Subject to any disclaimer, the term of this patent is extended or adjusted under 35 U.S.C. 154(b) by 36 days.

(21) Appl. No.: 15/251,009

(22) Filed: Aug. 30, 2016

(65) Prior Publication Data
US 2017/0248543 A1 Aug. 31, 2017

(30) Foreign Application Priority Data

Feb. 25, 2016 (FR) ...................................... 16 51570

(51) Int. Cl.
*H01L 27/07* (2006.01)
*G01N 27/414* (2006.01)
(Continued)

(52) U.S. Cl.
CPC ....... *H01L 27/0722* (2013.01); *G01N 27/414* (2013.01); *G01N 27/4145* (2013.01);
(Continued)

(58) Field of Classification Search
CPC ............ G01N 27/4145; H01L 27/0623; H01L 27/1203; H01L 29/42356; H01L 29/788;
(Continued)

(56) References Cited

U.S. PATENT DOCUMENTS

| 4,112,670 A | * | 9/1978 | Morozumi | ............... G04C 3/14 257/370 |
| 5,087,579 A | * | 2/1992 | Tomassetti | .......... H01L 27/0623 257/E27.015 |

(Continued)

FOREIGN PATENT DOCUMENTS

WO WO-2014204394 A1 12/2014

OTHER PUBLICATIONS

INPI Search Report and Written Opinion for FR 1651570 dated Feb. 2, 2017 (7 pages).
(Continued)

*Primary Examiner* — Scott B Geyer
(74) *Attorney, Agent, or Firm* — Crowe & Dunlevy

(57) ABSTRACT

An integrated electronic detector operates to detecting a variation in potential on an input terminal. The detector includes a MOS transistor having a drain forming an output. Variation in drain current is representative of the variation in potential. A bipolar transistor has a base forming the input terminal and a collector electrically connected to the gate of the MOS transistor. The detector has a first configuration in which the bipolar transistor is conducting and the MOS transistor is turned off. The detector has a second configuration in which the bipolar transistor is turned off and the MOS transistor is in a sub-threshold operation. Transition of the detector from the first configuration to the second configuration occurs in response to the variation in potential.

34 Claims, 1 Drawing Sheet

(51) Int. Cl.
  *H01L 27/06* (2006.01)
  *H01L 29/423* (2006.01)
  *G01R 19/165* (2006.01)
  *G01N 33/49* (2006.01)

(52) U.S. Cl.
  CPC .... *H01L 27/0623* (2013.01); *H01L 29/42356* (2013.01); *G01N 33/49* (2013.01); *G01R 19/16519* (2013.01)

(58) Field of Classification Search
  CPC ............... H01L 27/0259; H01L 27/102; H01L 27/1022; H01L 27/105; H01L 27/0711; H01L 27/0716; H01L 27/0722
  See application file for complete search history.

(56) References Cited

U.S. PATENT DOCUMENTS

| | | | | |
|---|---|---|---|---|
| 5,256,582 A * | 10/1993 | Mosher | H01L 27/0623 | 148/DIG. 9 |
| 5,296,409 A * | 3/1994 | Merrill | H01L 27/0623 | 257/E21.696 |
| 5,317,180 A * | 5/1994 | Hutter | H01L 21/761 | 257/327 |
| 5,572,048 A * | 11/1996 | Sugawara | H01L 27/0716 | 257/132 |
| 5,717,241 A * | 2/1998 | Malhi | H01L 27/0722 | 257/273 |
| 5,764,106 A * | 6/1998 | Deen | H01L 27/0722 | 257/E27.032 |
| 5,834,814 A * | 11/1998 | Ito | G05F 3/265 | 257/378 |
| 5,914,522 A * | 6/1999 | Aiello | H01L 27/0722 | 257/500 |
| 5,936,454 A * | 8/1999 | Joardar | H01L 27/0722 | 257/E27.032 |
| 6,071,768 A * | 6/2000 | Duvvury | H01L 27/0251 | 257/E27.032 |
| 6,787,850 B1 | 9/2004 | Pelloie | | |
| 7,989,875 B2 * | 8/2011 | Noort | H01L 27/0623 | 257/315 |
| 8,120,107 B2 * | 2/2012 | Terashima | H01L 27/0623 | 257/139 |
| 8,884,682 B2 * | 11/2014 | Nakahara | H01L 27/088 | 327/108 |
| 9,214,542 B2 * | 12/2015 | Chen | H01L 29/66659 | |
| 2002/0163366 A1 * | 11/2002 | Yamamoto | H01L 27/0623 | 327/110 |
| 2003/0111694 A1 * | 6/2003 | Terashima | H01L 27/0716 | 257/370 |
| 2004/0251517 A1 * | 12/2004 | Nakashima | H01L 21/8249 | 257/565 |
| 2007/0284672 A1 * | 12/2007 | Zafrani | H01L 27/0722 | 257/370 |
| 2009/0108346 A1 * | 4/2009 | Cai | H01L 27/0705 | 257/337 |
| 2009/0294799 A1 * | 12/2009 | Terashima | H01L 27/0248 | 257/139 |
| 2011/0108882 A1 * | 5/2011 | Terashima | H01L 27/0623 | 257/139 |
| 2011/0204455 A1 * | 8/2011 | Kang | G01N 27/4148 | 257/414 |
| 2013/0240744 A1 * | 9/2013 | Hurst, Jr. | H01L 31/119 | 250/370.05 |
| 2014/0017871 A1 | 1/2014 | Fenouillet-Beranger et al. | | |
| 2014/0252470 A1 * | 9/2014 | Chen | H01L 29/66659 | 257/337 |
| 2016/0153932 A1 * | 6/2016 | Eklund | G01N 27/414 | 257/253 |

OTHER PUBLICATIONS

Yuan, Heng et al: "MOSFET-BJT Hybrid Mode of the Gated Lateral Bipolar Junction Transistor for C-Reactive Protein Detection," Biosensors and Bioelectronics 28 (2011) 434-437.

* cited by examiner

HIGH-SENSITIVITY ELECTRONIC DETECTOR

PRIORITY CLAIM

This application claims priority from French Application for Patent No. 1651570 filed Feb. 25, 2016, the disclosure of which is incorporated by reference.

TECHNICAL FIELD

Various embodiments of the invention relate to integrated circuits and, more particularly, to integrated circuits capable of detecting small variations in electric potential induced, by way of a non-limiting example, by the detection of target molecules by a specific sensor in a 'lab-on-a-chip'.

BACKGROUND

A lab-on-a-chip conventionally comprises a molecular sensor connected to an electronic circuit configured for converting the data relating to the content of a fluid (a liquid or a gas) into electrical form. This data may be the presence or absence of a target molecule in the fluid, for example in the framework of a search for a virus in a sample of blood.

Lab-on-a-chip devices are known that use field-effect transistors, in which a molecular sensor is electrically connected to the gate of a transistor. Thus, the variation in potential induced by the detection of the target molecule of the sensor leads to a variation in the drain current of the transistor.

For example, for a variation in potential $V_G$ of 0.3 volts on the gate of a conventional field-effect transistor, the value of the drain current $I_{drain}$ of the transistor may be multiplied by $10^5$.

The slope factor of a transistor—also known by those skilled in the art under the term "sub-threshold swing"—is a value allowing the characterization of the voltage to be applied to the gate of an MOS transistor in order to make its drain current vary by a decade.

In this example, the slope factor of the transistor is equal to 60 mV/decade.

However, this value is too high for some applications, such as for example the detection of deoxyribonucleic acid (DNA) molecules, which require devices having a slope factor less than 60 mV/decade.

Lab-on-a-chip devices also exist that use advanced technologies, such as for example silicon nano-wires or carbon nanotubes, and which enable the fabrication of transistors having a lower slope factor.

However, the fabrication of devices integrating these technologies requires specific and complex methods, which are not yet suitable for industrialization.

SUMMARY

Thus, according to one embodiment, here, an integrated electronic detector is provided having a low value of slope factor, fabricated by conventional technologies and compatible with a technology of the FDSOI type.

According to one aspect, an integrated electronic detector is provided configured for detecting the appearance of a variation in potential on an input terminal, comprising an MOS transistor whose drain forms an output terminal, and in which the variation of the drain current is representative of the said variation in potential on the input terminal.

According to a general feature of this aspect, the sensor furthermore comprises a bipolar transistor whose base forms the input terminal and whose collector is electrically connected to the gate of the MOS transistor.

The detector also has a first configuration in which the bipolar transistor is conducting and the MOS transistor is turned off, and a second configuration in which the bipolar transistor is turned off and the MOS transistor is in a sub-threshold operation, with for example its gate floating. The detector is then configured for going from its first configuration to its second configuration when the said variation in potential occurs.

As is known to those skilled in the art, the sub-threshold operation of an MOS transistor is an operation in which a current may be measured flowing between the source and the drain of the transistor while the gate-source voltage is below the threshold voltage.

In the first configuration, the emitter of the bipolar transistor is for example negatively biased, and in the first and the second configurations, the drain of the MOS transistor is for example positively biased.

Thus, in the first configuration, which is the initial state, the base-emitter voltage of the bipolar transistor is for example slightly higher than its threshold voltage, which allows a conducting state of the transistor and hence the gate of the MOS transistor to be biased at substantially the same potential as the emitter of the bipolar transistor. Since this potential is negative, the MOS transistor is turned off.

A small variation in potential on the base of the bipolar transistor allows the bipolar transistor to be turned off, rendering the gate of the MOS transistor floating.

Thus, the stray field generated by the positive bias of the drain is no longer compensated by the negative bias of the gate, which leads to a large variation of the drain current, of the order of several decades. It should be noted that, since the MOS transistor is operating under its threshold voltage, this drain current remains lower than the drain current flowing in the MOS transistor in the conducting state.

The MOS transistor can be fabricated using a technology of the silicon-on-insulator type and comprising a buried secondary control electrode (commonly denoted by those skilled in the art under the term "back gate"), situated under the insulator and electrically coupled to the emitter of the bipolar transistor.

According to one embodiment, the detector comprises: a carrier substrate with a first type of conductivity comprising, in a first region, a first semiconductor well of a second type of conductivity; a buried insulating layer situated between the first well and a semiconductor film, the MOS transistor being situated within and on the semiconductor film, and the secondary control electrode situated under the buried insulating layer.

The carrier substrate comprises, in a second region, a second semiconductor well of the first type of conductivity forming the base of the bipolar transistor, a first region of the first type of conductivity, a second region of the second type of conductivity forming the collector of the bipolar transistor, an extension of the first semiconductor well forming the emitter of the bipolar transistor, and a metallization connecting the collector of the bipolar transistor to the gate of the MOS transistor.

The first type of conductivity is for example a conductivity of the P type and the second type of conductivity is for example a conductivity of the N type.

BRIEF DESCRIPTION OF THE DRAWINGS

Other advantages and features of the invention will become apparent upon examining the detailed description of non-limiting embodiments of the invention and from the appended drawings in which.

DETAILED DESCRIPTION

Figure 1:
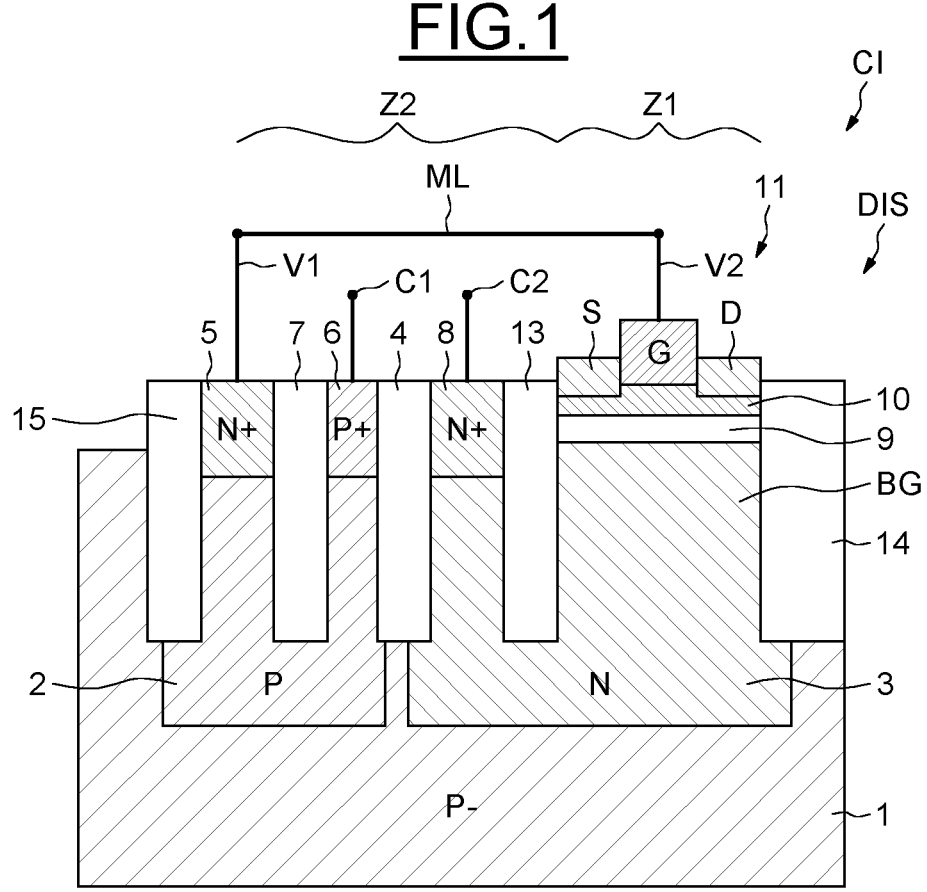
FIGS. 1 and 2 illustrate an embodiment of a detector circuit.

FIG. 1 illustrates an integrated circuit IC here generally comprising a substrate of the fully-depleted silicon-on-insulator type (or FDSOI, according to the acronym well known of those skilled in the art) conventionally comprising a carrier substrate 1, a buried insulating layer 9, and an intrinsic semiconductor film 10.

The integrated circuit IC here incorporates a detector DIS.

The carrier substrate 1 is a substrate of a first type of conductivity, for example here a substrate made of silicon with a light doping of the P type, and in which two regions Z1 and Z2 may be defined.

In the first region Z1, which is here bounded by two insulating regions, for example a first and a second deep trench isolation (known by the acronym DTI) 13 and 14, the detector comprises a first semiconductor well 3 having a second type of conductivity, for example the N type of conductivity, which is located under a part of the buried insulating layer 9.

The detector also comprises an MOS transistor, here an NMOS transistor 11, formed in this case within and on the film of fully-depleted silicon.

The source S and drain D regions are raised up and formed in a conventional manner within and on the film 10, by silicon epitaxy.

The gate G of the transistor conventionally comprises a layer of insulating material underneath a gate material.

This configuration in which the NMOS transistor 11 is situated on a semiconductor well of the same type of conductivity as the transistor, here a conductivity of the N type, is known by those skilled in the art under the term "Flip well".

In a second region Z2 of the substrate bounded by the first isolation trench 13 and a third isolation trench 15, the buried insulating layer 9 has been eliminated.

In this second region Z2, the upper portion of the first well 3 comprises an extension 8 insulated from the MOS transistor 11 by the trench 13. Furthermore, the detector DIS comprises, in this region Z2, a second buried semiconductor well 2, with P-type doping, a first upper portion of which is separated from the well extension 8 by a fourth deep isolation trench 4.

The isolation trench 4 has a depth chosen so as to allow a PN junction to subsist under it which is going to form part of a bipolar transistor, here of the NPN type, as will be explained hereinafter.

In this regard, although a space has been shown in the schematic FIG. 3 for the sake of clarity, under the isolation trench 4, the wells 2 and 3 are adjacent or sufficiently close to form an effective PN junction.

The detector comprises, in a second upper portion of the second well 2, a first highly doped region 5 of the N type and a second highly doped region 6 of the P type allowing a first contact C1 to be made enabling the second well 2 to be biased.

The two doped regions 5 and 6 are mutually separated by a fifth deep isolation trench 7.

A contact C2 allows the extension 8 of the first well 3 and the first well 3 itself to be biased.

It should be noted here that the second contact C2 allows the NMOS transistor 11 to be biased via its back face.

The MOS transistor therefore has a buried secondary control electrode or second gate, referred to as "back gate" BG, situated under the buried insulating layer 9.

The integrated circuit IC conventionally comprises an interconnection part situated on top of the substrate and comprising several metallization levels and vias. This interconnection part is commonly denoted by those skilled in the art as "BEOL" (for Back End Of Line).

The first highly doped region 5 is here electrically connected to the gate G of the NMOS transistor 11 via an electrical link comprising a metal track ML and vias V1 and V2 situated within the said interconnection part.

Figure 2:
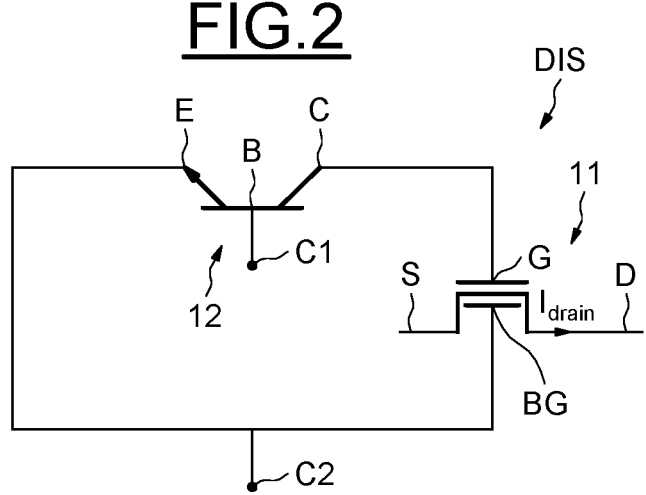

A schematic representation of the circuit from an electrical standpoint is illustrated in FIG. 2.

The NMOS transistor 11 is shown in the figure, comprising its drain D, source S and gate G regions.

The junctions between the second well 2, the first highly doped region 5, and the first well 3 form a bipolar transistor 12, here an NPN transistor, whose first doped region 5 is the collector C, whose second well 2 is the base B, and whose extension of the first well 3 is the emitter E.

The emitter E is therefore connected to the back gate BG of the MOS transistor 11, and the collector C to the main gate G of the NMOS transistor 11.

Thus, the first contact C1 allows the base B of the bipolar transistor 12 to be biased, and the second contact C2 allows the emitter E of the bipolar transistor 12 and the back gate BG of the NMOS transistor 11 to be simultaneously biased.

In operation, the circuit may advantageously be used in a lab-on-a-chip. In this case, the first contact C1, in other words the base of the bipolar transistor, is used as an input terminal of the sensor, and the drain D of the NMOS transistor 11 is used as an output terminal.

For example, the first contact C1 may be electrically connected to a molecular sensor, comprising for example and conventionally a functionalized electrode comprising a functionalized metal layer comprising a material capable of attaching itself to a target molecule, and optionally a dielectric layer under the said metal layer.

When a molecule attaches itself to the sensor, an electrical charge is generated in the sensor making the potential of the base B vary. This variation in potential depends notably on the nature of the molecule to be detected.

The drain D of the NMOS transistor 11 may for example be connected to a read circuit.

In this example, the first contact C1, in other words the base B of the bipolar transistor, is initially at a potential $V_{C1}$ of zero, which corresponds to the absence of a molecule on the sensor.

The drain D of the MOS transistor is biased, for example at a potential of 0.6 volts.

This bias of the drain D generates a stray field within the channel, and the drain then acts as a spurious gate. This phenomenon, known to those skilled in the art by the term "fringing field", is conventional in MOS transistors of the silicon-on-insulator type.

Adjusting the potential of the second contact C2, in other words of the emitter of the bipolar transistor 12 and of the back gate BG of the NMOS transistor 11, in such a manner that the base-emitter voltage is initially slightly higher than the threshold voltage of the bipolar transistor so as to render it conducting, while at the same time only allowing a small variation in potential on the base of the bipolar transistor 12, leads to a change of its state.

Thus, since the threshold voltage of the bipolar transistor 12 is in this example 0.6V, the potential of the second contact $V_{C2}$ is here fixed at −0.65V volts. Since the potential of the base is initially zero, the base-emitter voltage is 0.65V and therefore above the threshold voltage. The bipolar transistor 12 is therefore initially in a conducting state, and the gate G of the transistor 11 is therefore negatively biased.

Initially, the detector is therefore in a first configuration in which the bipolar transistor 12 is conducting and the NMOS transistor 11 is turned off owing to the negative bias on its gate G.

Only a very low leakage current flows in the drain, for example here a current $I_{drain}$ with a value of $10^{-10}$ amps.

It should be noted here that, since the emitter E of the bipolar transistor 12 is electrically connected to the back gate BG of the MOS transistor, the latter is also negatively biased at a potential of −0.65V. However, the effect of the bias of the back gate on the channel with respect to that of the bias of the main gate is negligible.

When there is a variation of the potential $V_{C1}$ on the base B of the bipolar transistor 12, for example a variation of +0.1 volts, due to the attachment of one or more molecules onto the sensor, the base-emitter voltage of the bipolar transistor 12 goes from 0.65 volts to 0.55 volt. The base-emitter voltage is therefore lower than the threshold voltage of the bipolar transistor.

The detector therefore goes into a second configuration in which the bipolar transistor 12 is turned off, and the gate G of the MOS transistor 11 is no longer biased. The gate of the MOS transistor therefore becomes floating.

Thus, in the absence of a bias on the main gate, the fringing field generated by the biasing of the drain leads to a significant increase in the conduction of the MOS transistor. The MOS transistor is therefore here in a sub-threshold operation.

In this example, the drain current $I_{drain}$ reaches a value of $10^{-4}$ amp, this being an increase of 6 decades.

Thus, for a small variation of the potential $V_B$ on the base of the bipolar transistor, a large variation in drain current $I_{drain}$ is obtained. Here, the slope factor of the circuit is 11 mV/decade, which is much lower than the value obtained with devices of the prior art fabricated with conventional technologies.

It should be noted that the embodiments presented here are non-limiting.

The fact that the emitter of the bipolar transistor is electrically connected to the back gate of the MOS transistor is due here to the method of fabrication of the integrated circuit and does not influence the operation of the sensor. It would therefore be perfectly possible to envisage a detector in which the emitter and the back gate are mutually isolated, or else a detector in which the MOS transistor were formed using a "bulk" technology with the emitter of the bipolar transistor isolated from the substrate of the MOS transistor.

Furthermore, although an embodiment has been described here in which the potential of the second contact C2 is fixed in order to detect a variation in potential on the first contact C1, an embodiment in which the potential of the second contact C2 might be varied in order to search for the value for which the device goes from the first configuration to the second configuration could also be envisaged.

In this case, depending on the value of potential for which this change of configuration were observed, in other words a significant increase in the drain current $I_{drain}$, the presence or the absence of molecules on the sensor would be deduced.

It would also be possible to have an integrated circuit in which the carrier substrate 1 would be more highly doped, with a doping identical to that of the second well 2. Thus, it would be possible to make the contact with the first contact C1 on the carrier substrate, for example on its back face.

Lastly, although the invention is advantageously applicable to the field of lab-on-a-chip devices, its use in any other field requiring the detection of the appearance of small variations in potential could very well be envisaged, by for example connecting the contact C1 to a different sensor other than a molecular sensor.

The invention claimed is:

1. An integrated circuit, comprising:
   a MOS transistor having a gate, a drain, a source and a back gate that is provided by a semiconductor region insulated from said drain and source by an insulating layer; and
   a bipolar transistor having a base, a collector that is electrically connected to the gate of the MOS transistor, and an emitter that is electrically connected to the back gate of the MOS transistor.

2. The integrated circuit of claim 1, further a biasing of the drain and emitter at potentials which cause the bipolar transistor to be conducting and the MOS transistor to be turned off in the absence of a certain amount of charge at the base.

3. The integrated circuit of claim 2, wherein the certain amount of charge at the base causes the bipolar transistor to be turned off and the MOS transistor to have a sub-threshold operation.

4. The integrated circuit of claim 3, wherein the gate of the MOS transistor is floating when the bipolar transistor is turned off.

5. The integrated circuit of claim 2, wherein the means for biasing causes the emitter of the bipolar transistor to be biased negatively and the drain of the MOS transistor to be biased positively.

6. The integrated circuit of claim 1, wherein the back gate and emitter are formed by a same doped portion of the semiconductor region.

7. The integrated circuit of claim 1, further comprising a metal line that directly electrically connects the collector of the bipolar transistor to the gate of the MOS transistor.

8. An integrated circuit, comprising:
   a first semiconductor substrate layer;
   an insulating layer on the first semiconductor substrate layer; and
   a second semiconductor substrate layer on the insulating layer,
   a MOS transistor having a gate, a drain, a source and a back gate; and
   a bipolar transistor having a base, a collector that is electrically connected to the gate of the MOS transistor, and an emitter that is electrically connected to the back gate of the MOS transistor,
   wherein said source and drain are formed at least in the second semiconductor substrate layer, and wherein said back gate and emitter are formed by a first doped region within the first semiconductor substrate layer.

9. The integrated circuit of claim 8, further comprising a second doped region within the first semiconductor layer, said first and second doped regions being adjacent to each other and having opposite doping type.

10. The integrated circuit of claim 9, wherein the base is formed by said second doped region and further comprising a third doped region within the second doped region and oppositely doped from the second doped region, said collector formed by said third doped region.

11. The integrated circuit of claim 10, further including a fourth doped region of a same doping type as the second doped region forming a base contact for the bipolar transistor, wherein said third and fourth doped regions are separated from each other by an insulating region.

12. The integrated circuit of claim 11, wherein the fourth doped region is separated from the first doped region by a further insulating region.

13. An integrated electronic detector configured for detecting a variation in potential on an input terminal and comprising:
an MOS transistor having a drain forming an output terminal, wherein a variation of drain current is representative of variation in potential on the input terminal;
a bipolar transistor having a base forming the input terminal and having a collector that is electrically connected to the gate of the MOS transistor;
wherein the integrated electronic detector has a first configuration in which the bipolar transistor is conducting and the MOS transistor is turned off, and has a second configuration in which the bipolar transistor is turned off and the MOS transistor is in a sub-threshold operation, the integrated electronic detector being configured for going from the first configuration to the second configuration in response said variation in potential on the input terminal.

14. The integrated electronic detector according to claim 13, wherein the gate of the MOS transistor is floating in the second configuration.

15. The integrated electronic detector according to claim 14, wherein the emitter of the bipolar transistor is biased negatively in the first configuration, and the drain of the MOS transistor is positively biased in the first configuration and the second configuration.

16. The integrated electronic detector according to claim 13, wherein the MOS transistor is fabricated using a silicon-on-insulator type substrate and comprises a secondary buried control electrode situated under an insulator, said buried control electrode electrically coupled to the emitter of the bipolar transistor.

17. The integrated electronic detector according to claim 16, wherein the silicon-on-insulator type substrate comprises a carrier substrate of a first type of conductivity comprising:
in a first region, a first semiconductor well of a second type of conductivity, a buried insulating layer situated between the first semiconductor well and a semiconductor film, wherein the MOS transistor is situated within and on the semiconductor film and the secondary control electrode is situated under the buried insulating layer; and
in a second region, a second semiconductor well of the first type of conductivity forming the base of the bipolar transistor, a first region of the first type of conductivity, a second region of the second type of conductivity forming the collector of the bipolar transistor, an extension of the first semiconductor well forming the emitter of the bipolar transistor.

18. The integrated electronic detector of claim 17, further comprising a metallization connecting the collector of the bipolar transistor to the gate of the MOS transistor.

19. The integrated electronic detector according to claim 17, wherein the MOS transistor is an NMOS transistor, the first type of conductivity is a conductivity of the P type, and the second type of conductivity is a conductivity of the N type.

20. An integrated circuit, comprising:
a MOS transistor having a gate, a drain, a source and a back gate that is provided by a semiconductor region insulated from said drain and source; and
a bipolar transistor having a base, a collector that is electrically connected to the gate of the MOS transistor, and an emitter that is electrically connected to the back gate of the MOS transistor,
wherein the emitter is formed by said semiconductor region providing the back gate of the MOS transistor.

21. The integrated circuit of claim 20, further a biasing of the drain and emitter at potentials which cause the bipolar transistor to be conducting and the MOS transistor to be turned off in the absence of a certain amount of charge at the base.

22. The integrated circuit of claim 21, wherein the certain amount of charge at the base causes the bipolar transistor to be turned off and the MOS transistor to have a sub-threshold operation.

23. The integrated circuit of claim 22, wherein the gate of the MOS transistor is floating when the bipolar transistor is turned off.

24. The integrated circuit of claim 21, wherein the means for biasing causes the emitter of the bipolar transistor to be biased negatively and the drain of the MOS transistor to be biased positively.

25. An integrated circuit, comprising:
a MOS transistor having a gate, a drain, a source and a back gate; and
a bipolar transistor having a base, a collector that is electrically connected to the gate of the MOS transistor, and an emitter that is electrically connected to the back gate of the MOS transistor,
wherein the back gate and emitter are formed by a same doped semiconductor region.

26. The integrated circuit of claim 25, further a biasing of the drain and emitter at potentials which cause the bipolar transistor to be conducting and the MOS transistor to be turned off in the absence of a certain amount of charge at the base.

27. The integrated circuit of claim 26, wherein the certain amount of charge at the base causes the bipolar transistor to be turned off and the MOS transistor to have a sub-threshold operation.

28. The integrated circuit of claim 27, wherein the gate of the MOS transistor is floating when the bipolar transistor is turned off.

29. The integrated circuit of claim 25, wherein the means for biasing causes the emitter of the bipolar transistor to be biased negatively and the drain of the MOS transistor to be biased positively.

30. An integrated circuit, comprising:
a MOS transistor having a gate, a drain, a source and a back gate;
a bipolar transistor having a base, a collector that is electrically connected to the gate of the MOS transistor, and an emitter that is electrically connected to the back gate of the MOS transistor; and
a metal line that directly electrically connects the collector of the bipolar transistor to the gate of the MOS transistor.

31. The integrated circuit of claim 30, further a biasing of the drain and emitter at potentials which cause the bipolar transistor to be conducting and the MOS transistor to be turned off in the absence of a certain amount of charge at the base.

32. The integrated circuit of claim 31, wherein the certain amount of charge at the base causes the bipolar transistor to be turned off and the MOS transistor to have a sub-threshold operation.

33. The integrated circuit of claim 32, wherein the gate of the MOS transistor is floating when the bipolar transistor is turned off.

34. The integrated circuit of claim 31, wherein the means for biasing causes the emitter of the bipolar transistor to be biased negatively and the drain of the MOS transistor to be biased positively.

* * * * *